(12) United States Patent
Hatzianestis

(10) Patent No.: US 9,980,057 B2
(45) Date of Patent: May 22, 2018

(54) PREDICTIVE POWER ADJUSTMENT IN AN AUDITORY PROSTHESIS

(75) Inventor: Kostas Hatzianestis, Elizabeth Bay (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days. days.

(21) Appl. No.: 13/553,804

(22) Filed: Jul. 19, 2012

(65) Prior Publication Data

US 2014/0023215 A1    Jan. 23, 2014

(51) Int. Cl.
*H04R 25/00* (2006.01)
*A61N 1/36* (2006.01)

(52) U.S. Cl.
CPC ....... *H04R 25/505* (2013.01); *A61N 1/36036* (2017.08); *H04R 2460/03* (2013.01)

(58) Field of Classification Search
USPC .................................................. 381/380, 151
See application file for complete search history.

(56) References Cited

U.S. PATENT DOCUMENTS

| | | | |
|---|---|---|---|
| 5,741,314 A | 4/1998 | Daly et al. | |
| 5,876,425 A | 3/1999 | Gord et al. | |
| 5,949,484 A * | 9/1999 | Nakaya et al. | 348/384.1 |
| 6,537,200 B2 * | 3/2003 | Leysieffer et al. | 600/25 |
| 8,144,908 B2 | 3/2012 | Asnes | |
| 2004/0131214 A1 * | 7/2004 | Galler | H04R 25/505 |
| | | | 381/323 |
| 2004/0247148 A1 * | 12/2004 | Pedersen | 381/323 |
| 2005/0094834 A1 * | 5/2005 | Chalupper | H04R 25/407 |
| | | | 381/313 |
| 2006/0184213 A1 | 8/2006 | Griffith | |
| 2007/0118185 A1 | 5/2007 | Shaquer | |
| 2008/0132750 A1 * | 6/2008 | Miller | 600/25 |
| 2013/0129125 A1 * | 5/2013 | Meskens | H04R 25/606 |
| | | | 381/314 |
| 2016/0044427 A1 | 2/2016 | Meskens et al. | |

FOREIGN PATENT DOCUMENTS

| | | |
|---|---|---|
| KR | 10-0573622 B1 | 4/2006 |
| WO | 0180795 A1 | 11/2001 |
| WO | 2013076653 A2 | 5/2013 |

OTHER PUBLICATIONS

International Search Report. PCT/IB2013/055887, dated Mar. 12, 2014.
Partial Supplemental European Search Report dated Feb. 17, 2016 in European Application No. 3820371.6-1901.
Extended European Search Report dated Jun. 6, 2016 in European Application No. 13820371.6-1901.
European Exam Report issued in counterpart European Application No. 13820371.6, dated Jan. 4, 2018, 6 pages.

* cited by examiner

*Primary Examiner* — Amir Etesam

(57) ABSTRACT

In an auditory prosthesis having an external unit and an internal unit for implantation in a recipient, a method of operation includes: characterizing an acoustic signal received by the auditory prosthesis; adjusting at least one parameter of the auditory prosthesis based on the characterized acoustic signal; and processing the acoustic signal to provide an encoded signal for transmission to the internal unit; wherein an amount of energy transmitted in the encoded signal depends on the at least one parameter.

27 Claims, 7 Drawing Sheets

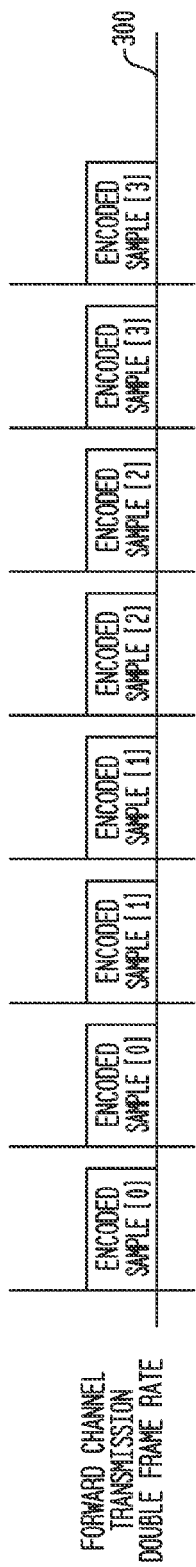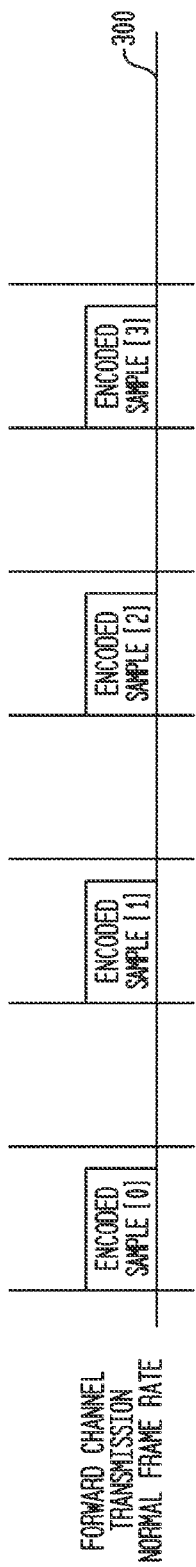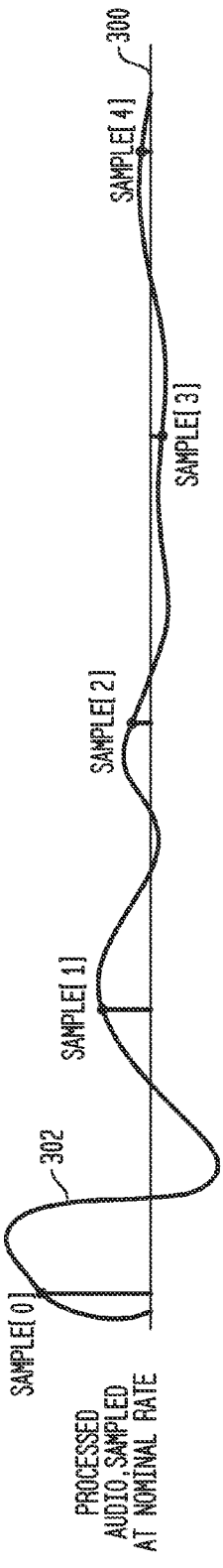

PREDICTIVE POWER ADJUSTMENT IN AN AUDITORY PROSTHESIS

BACKGROUND

The present disclosure relates generally to the provision of power to an implanted medical device, and more particularly, to the provision of power to an auditory prosthesis.

Many implantable medical devices, such as auditory prostheses, are active implantable medical devices (AIMDs) which consume power. Such devices require power to be transferred from an external unit to an implanted unit. More recently, this transfer of power is generally performed transcutaneously since percutaneous leads may cause discomfort to and may be a potential source of infection.

The electronics in an auditory prosthesis typically consumes a small portion of the total electrical power consumed by the implantable unit of the prosthesis. The auditory prosthesis' components which are involved in sound amplification and generation consume the largest proportion of the implant's available power. Their power characteristic is generally dependent on the instantaneous sound intensity that is required during the implant's operation.

The radio-frequency (RF) signal sent to the implanted unit transfers energy that is used to power the implanted unit. Intermittencies can occur in the implanted unit's operation if insufficient power is transmitted to the implanted unit. On the other hand, excessive power can be consumed in the implanted unit if the power-determining parameters are too high. The intermittencies are the result of temporal modulations in the implanted unit's unregulated voltage, which technical represent an imbalance between power supplied to the implant and actual load demand.

The power in the RF signal is adjusted to avoid underpowering the implanted unit, i.e., to try to maintain a sufficient energy margin in the implant's tank capacitance and regulator. The power in the RF signal also is adjusted to avoid transients that overpower the implanted unit, i.e, to avoid circumstances in which the implanted unit's overvoltage protection circuits are in conduction.

A measurement of the implant's unregulated voltage and current, in some cases, is telemetered back periodically to the external speech processor (SP) to assist in the power level adjustment of the RF (carrier amplitude at resonance).

SUMMARY

According to an embodiment of the present disclosure, in an auditory prosthesis having an external unit and an internal unit for implantation in a recipient, a method of operating the same includes: characterizing an acoustic signal received by the auditory prosthesis; adjusting at least one parameter of the auditory prosthesis based on the characterized acoustic signal; and processing the acoustic signal to provide an encoded signal for transmission to the internal unit; wherein an amount of energy transmitted in the encoded signal depends on the at least one parameter.

According to another embodiment of the present disclosure, an auditory prosthesis comprises an external unit and an internal unit, the latter being implantable in a recipient. The external unit includes: a microphone to capture a sound signal; a sound processor to characterize acoustic behaviour of the sound signal and generates an encoded signal representative thereof; and an RF transmitter to transmit an RF signal according to the encoded signal. The internal includes: a receiver to receive the RF signal and to extract energy therefrom for powering the internal unit; a decoder that decodes data from the transmitted signal; and an actuator that stimulates the recipient's auditory system based on the decoded data. The external unit further includes a controller to adjust at least one parameter of the prosthesis that affects power consumption based on the characterized sound signal.

BRIEF DESCRIPTION OF THE DRAWINGS

FIGS. 5A-C illustrate a method, according to another embodiment of the present disclosure, in which the frame rate transmitted from the external unit to the internal unit 5 of an auditory prosthesis is adapted/varied according to the instantaneous sound intensity and predicted demand in the internal unit's electrical power;

DETAILED DESCRIPTION

The present disclosure is generally directed to dynamically predicting the power demand of an implantable, internal unit of an auditory prosthesis based on characteristics of a received sound, and to dynamically adjust prosthesis parameters in anticipation of higher or lower power demand in the internal unit, in particular its actuator(s).

Figure 1:
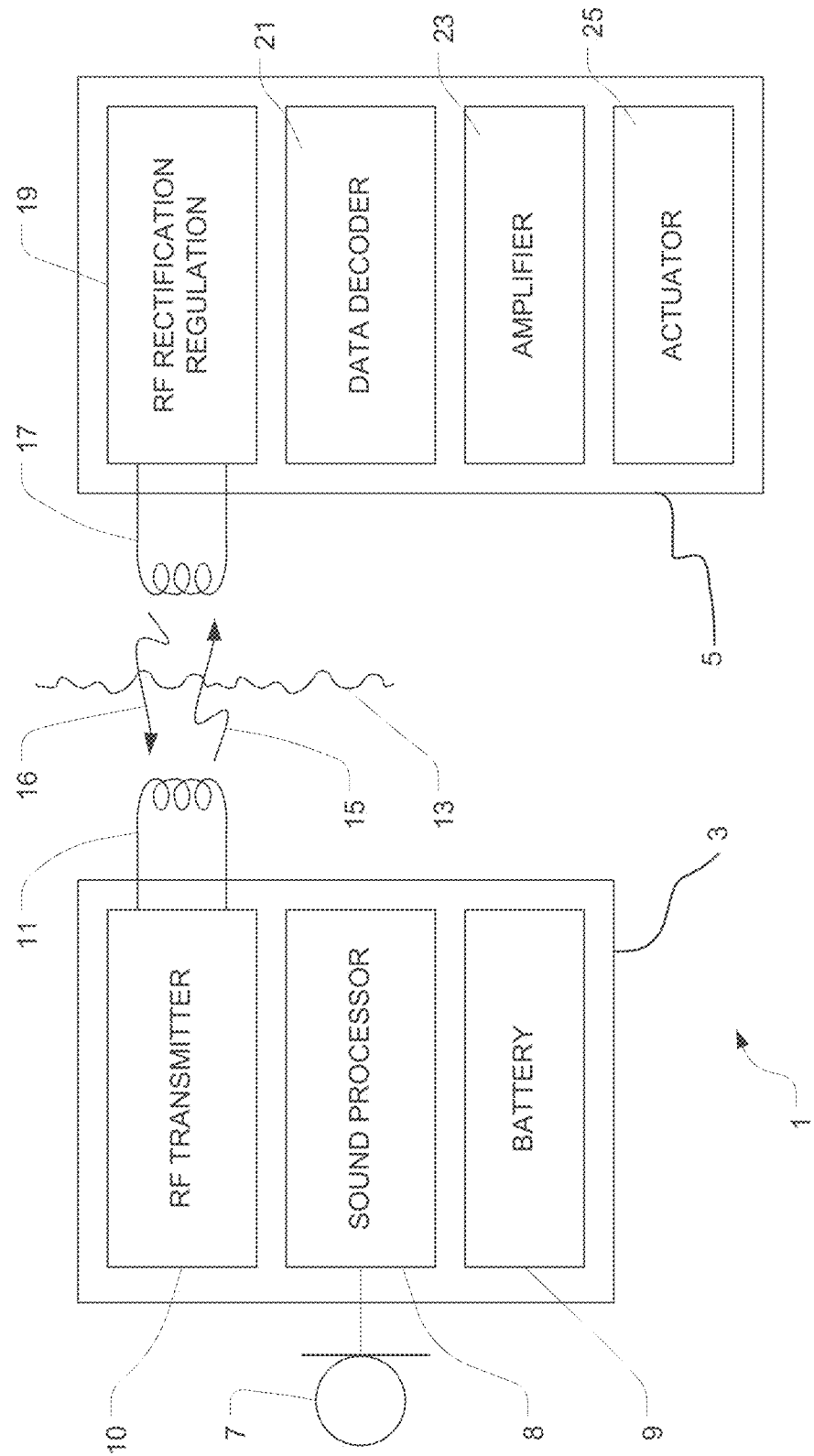
FIG. 1 is a simplified block diagram of an auditory prosthesis, according to an embodiment of the present disclosure.

FIG. 1 is a simplified block diagram of an auditory prosthesis 1, according to an embodiment of the present disclosure. In FIG. 1, the auditory prosthesis 1 includes an external unit 3 and an implantable internal unit 5. External unit 3 has a microphone 7, a sound processor 8 and a radio frequency (RF) transmitter 10. Auditory prosthesis 1 is powered by a battery 9 located in the external unit 3. A voltage regulator (not shown) controls the voltage supplied to the sound processor 8 and RF transmitter 10. Since the external unit 3 is typically worn behind the recipient's ear, there is a constraint on the size and weight of the external unit. Consequently there is a need for efficient usage of the power generated by battery 9.

The RF transmitter 10 transmits a radio frequency signal 15 through the recipient's skin 13, using inductively coupled external and internal coils 11 and 17, respectively. The RF signal 15 is received by the internal coil 17 that is located so as to enable inductive coupling with the external coil 11, and provided in some form to other components of the internal unit 5 of prosthesis 1. In some arrangements, an RF signal 16 is also transmitted from the internal unit 5 to the external unit 3, for example to provide information about the status of the internal unit 5.

FIG. 1 illustrates some functional units of the implantable part 5, including circuitry 19 that rectifies and regulates the received RF signal 15. As described below with reference to FIG. 3, the energy received via the received RF signal 15 serves to charge up a task capacitor 104 (see FIG. 3, discussed below) that is used to power the internal unit 5.

The internal unit 5 also includes a data decoder 21; an amplifier 23; and an actuator 25. The data decoder 21 extracts the data which is encoded in the received RF signal 15. The amplifier 23 drives the actuator 25 based on the decoded data. The actuator 25 may, for example, include an array of electrodes (not illustrated) that stimulate the auditory nerve of the cochlea. In other arrangements, the actuator 25 may be an electro-acoustical transducer, or an electro-mechanical transducer that generate a linear movement to provide mechanical stimulation. For example, an electromechanical instance of the actuator 25 may be implanted in the middle ear, with a diaphragm that acts to move the fluid in the cochlea to stimulate the cochlea and auditory nerve. In some arrangements, the actuator 25 may be an electromechanical transducer that impart mechanical vibrations to the bone of the recipient's skull, with the bone transmitting the vibrations by conduction to the inner ear.

Figure 2:
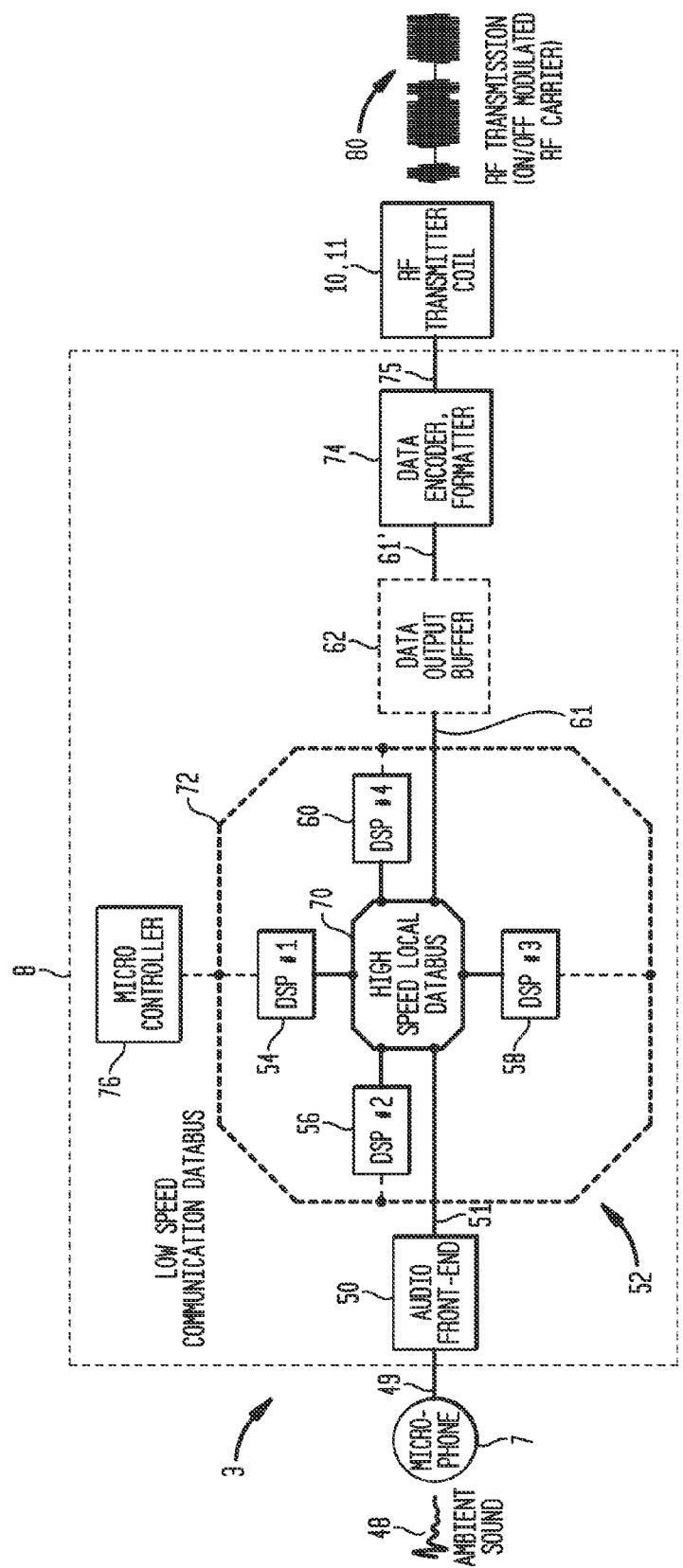
FIG. 2 is a schematic block diagram, according to another embodiment of the present disclosure, illustrating an external unit of an auditory prosthesis, e.g., the prosthesis illustrated in FIG. 1.

FIG. 2 is a schematic block diagram, according to another embodiment of the present disclosure, illustrating an external unit of an auditory prosthesis, e.g., the external unit 3 of the auditory prosthesis 1 of FIG. 1. In an auditory prosthesis, received ambient sound 48 is converted into an electrical signal by the microphone 7, which is digitally processed/analysed by the sound processor 8 to generate control signals which are provided to the internal unit 5 via the noted induction link. In response to these control signals, the internal unit 5 generates acoustic, mechanical and/or electrical stimulation signals which are delivered by the actuator 25 to cause a hearing percept. The total time, from the point of capturing the sound to causing the hearing percept, is referred to as the group delay of the auditory prosthesis. It is advantageous for the group delay not to exceed 10 ms so that the hearing percepts induced by the auditory prosthesis do not suffer a discernable phase lag relative to the recipient's observations of a speaker's lip movements, which otherwise would compromise the recipient's lip-reading ability.

As noted, the sound 48 is captured by microphone 7. An audio front-end block 50 of sound processor 8 amplifies and filters the electrical audio signal 49 generated by microphone 7 against unwanted noise and converts the signal 49 from analog to digital form thereby generating a digital signal 51. The microphone 7 can be a bi-directional microphone or a microphone array/cluster that is used to achieve a fixed directionality, or beam-former-like adaptive directionality. In some embodiments, the sound signal 48 can be sampled, e.g., equidistantly, in the time-domain such that the sampling rate is at least double the maximum anticipated signal bandwidth. For example, a fixed data quantization (bit-width) can be used. The audio samples may be stored in an intermediate data buffer (not illustrated) that resides within audio front-end 50, or in another suitable remote data buffer.

The digital signal 51 is then processed by a cluster 52 of signal processors that implement various algorithms, for example (and, e.g., in order of a sequential execution): a) time-domain pre-processing, b) sound intensity based power level estimation, c) signal channelization via frequency analysis and d) feature extraction of the audio signal. In the illustrated example of FIG. 2, the cluster 52 includes four digital signal processors (DSPs) 54, 56, 58, 60. The DSPs 54-60 operate, e.g., concurrently, to execute, e.g., the above-noted four types of processing algorithms, and exchange data via a data bus 70. A supervising microcontroller 76 programs and configures in real-time the parameterization of the DSPs 54-60 via a data bus 72. On a relative basis, data bus 70 is higher speed as compared to data bus 72. For example, data bus 70 can be a time-shared high-speed bit-parallel data bus, whereas data bus 72 can be a low-speed bit-parallel or serial interface 72. The audio data processed by the DSP cluster 52 is output as a signal 61 and may be stored in an optional (as denoted by phantom lines) output buffer 62.

A data encoder and formatter 74 receives the processed audio data as a signal 61' from the output buffer 62 at a frame rate that is programmed by the supervising microcontroller 76. These quantized digital data are broken up into chunks of data bits that are individually mapped into appropriately defined data bit combinations with higher code disparity. The data formatter block 74 adds protection bits to the final bit combinations, and the prepared data stream 75 is serially transmitted by the RF transmitter 10 that includes a tuned circuit (not illustrated) and the RF coil 11. The transmitted RF signal 80 in the illustrated example is an on/off modulated RF carrier.

Figure 3:
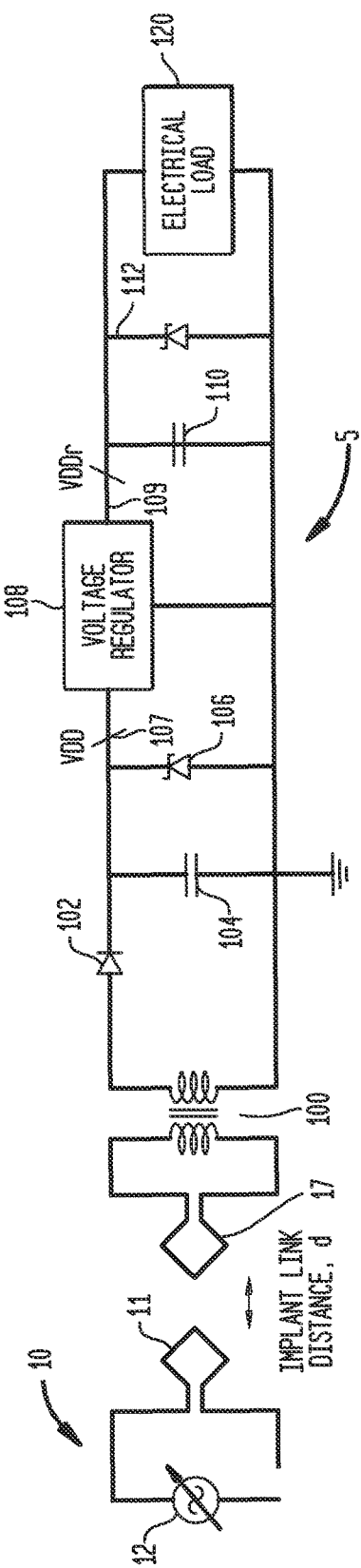
FIG. 3 is a simplified circuit diagram, according to another embodiment of the present disclosure, of the prosthesis of FIG. 1 illustrating the RF rectification and regulation functional block in an implantable unit of the prosthesis.

FIG. 3 is a simplified circuit diagram, according to another embodiment of the present disclosure, illustrating selected hardware blocks that are involved in the transfer of electrical power from an external unit of an auditory prosthesis to an internal unit thereof, e.g., from the external unit 3 to the internal unit of the auditory prosthesis 1.

The RF transmitter 10 includes an RF source 12 (generating a carrier signal, e.g, at 5 MHz) connected to the transmitter coil 11. RF transmitter 12 operates with an electrical voltage that varies over time as battery energy is depleted in the external unit 3. The external unit 3 includes a mechanism to adjust the Power Level (PL) of the RF carrier, expressed in percentage ranges from, e.g., 50 to 100%. In one arrangement, the sound-intensity-based power level estimation results in a power level adjustment being made to pulse width modulation of the signal that is used to excite the tuned circuit in the transmitter block. The sound-intensity-based power level estimation and the resulting power level adjustment are implemented, for example as algorithms (e.g., dedicated algorithms) in the DSP cluster 52.

The separation distance between the external and internal coils 11 and 17, respectively, is determined by the recipient's skin flap thickness and is typically between about 0 mm to about 10 mm. This separation distance affects the transfer of electrical energy to the internal unit 5 (link efficiency k) and modulates the electrical voltage that is generated in the internal unit 5. The skin flap thickness is determined during surgery and is confirmed during the initial programming session for each recipient individually, for example by examining the correctness of the implant's telemetry over a power level range. The skin flap thickness is used as a primary variable in the real-time calculation of the power level setting (e.g., see block 207 discussed below) based on the instantaneous sound intensity.

The internal unit 5 extracts the electrical energy that is necessary to sustain its essential functionality by rectifying the received RF signal, using a transformer 100 and a diode 102, and storing the extracted energy in a tank capacitor 104. The voltage across the tank capacitor is denoted $V_{DD}$, and represents the unregulated voltage 107 of the internal unit 5. The unregulated voltage 107 is stabilized by a voltage regulator 108 so that the data decoder 21, the amplifier 23 and the actuator 25 operate with substantially constant supply voltages. The output voltage 109 of regulator 108 is denoted $V_{DDr}$ and represent the regulated voltage of the internal unit 5.

A primary voltage protection diode 106, e.g., a zener diode, is provided between the input of the voltage regulator 108 and the electrical ground of internal unit 5. The diode 106 shunts excess voltages that might be generated by external sources to a level that is considered safe for the operation of the internal unit 5. The shunted energy may be a significant contributor to the electrical power losses suffered by the internal unit 5. The sound-intensity-based power level estimation provides a power level adjustment such that the unregulated voltage 107 is maintained at or below the breakdown region of the tester diode 106. The diode's characteristic relating electrical current to voltage shunting is non-linear. Generally, the conduction characteristic of zener diode 106 varies from due to manufacturing-related tolerances. In embodiments in which the diode 106 is a zener diode, the typical tolerance is +/− about 5% around the diode's rated breakdown voltage.

An output capacitor 110 is provided between the output of voltage regulator 108 and electrical ground. A secondary voltage protection diode 112 is provided in parallel with output capacitor 110. The regulated voltage 109 drives electrical load 120, which includes the data decoder 21, amplifier 23 and actuator 25.

Figure 4:
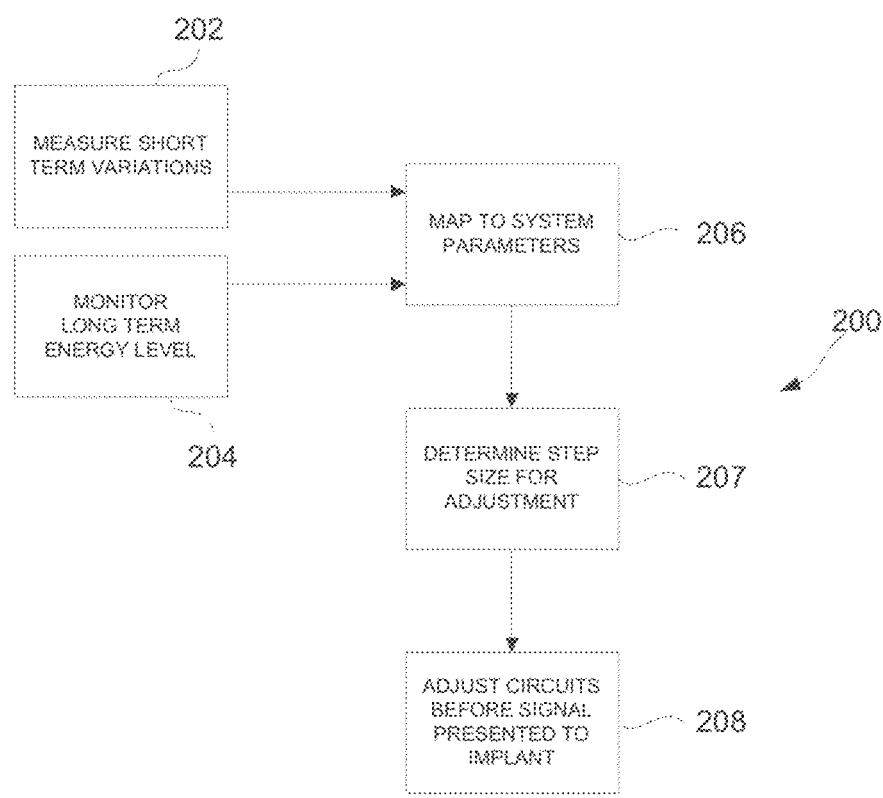
FIG. 4 is a flow chart illustrating a method, according to another embodiment of the present disclosure, of adjusting system parameters of an auditory prosthesis in anticipation of higher or lower power demand is the implant.

FIG. 4 is a flow chart illustrating a method 200, according to another embodiment of the present disclosure, that that may be implemented to predict power demand of auditory prosthesis based on the characteristics of the received ambient sound 48, and dynamically adjust system parameters in anticipation of the predicted power demand in the internal unit of the auditory prosthesis, e.g., in the internal unit 5 of the auditory prosthesis 1.

At block 202, an on-going process is performed by sound processor 8 to measure the onset of transient events in the audio signal 49 that may indicate a possible change in the intensity (short-term variations) of the sound signal 48. At block 204, the sound processor 8 monitors the long-term energy level of the audio signal 49 in the processing pipeline of external sound processor 8. Blocks 202 and 204 are implemented, e.g., by digital software or firmware in sound processor 8 operating on time- or frequency-domain compound or channelised audio information according to the algorithms which are implemented in one or more of the DSP units 54-60, e.g., the DSP units 54 and 56. As an example, in an all-digital implementation, the transient detection is based on a differentiator digital filter that operates in the time-domain and processes low-pass filtered audio samples. The low-pass filter is, e.g., a finite-impulse response type of digital filter that exhibits an out-of band attenuation of at least about 60 dB, pass-band ripple of about 3 dB, and has a transition bandwidth of about $\frac{1}{10}^{th}$ that of the filter's overall bandwidth. For execution economy, the filter can be implemented as a multi-rate filter using sub-sampling and effective reduction of the bandwidth in the audio signal's band of interest. The estimation techniques of blocks 202 and 204 can be also implemented, e.g., using temporal features extracted from the audio signal using a frequency estimation method such as a digital Fourier transform (FFT), multirate filterbank, wavelet transform, etc.

In block 206, algorithms operating in one of the DSP units 54-60, e.g., the DSP cluster 58, map the measured short-term and long-term intensities to derive appropriate settings for one or more system parameters. In block 207, a suitable increment size for a change in configuration parameters may be determined, as discussed in more detail below. In block 208, the configuration parameters of the auditory prosthesis 1 are adjusted in real-time according to the derived parameter settings and step sizes. The adjustment is performed in anticipation of the power demand in the internal unit 5, before the audio signal is presented to the data decoder 21, the amplifier 23 and actuator 25.

Method 200 thus provides the dynamic adjustment of configuration parameters of the auditory prosthesis 1 that impact the total power consumption and efficiency as a function of a predicted intensity and transient characteristic of the sound 48. The configuration parameters of the implant system that may be dynamically adjusted include: the amplitude of the RF carrier provided by the RF source 12 and used by the RF transmitter 10; the on/off duty cycle of the RF signal 80; the output voltage of the voltage regulator (not illustrated) serving the sound processor 8 and the RF transmitter 10; the rate at which RF frames are transmitted from the external unit 3 to the internal unit 5; and the quantisation (bit-width) and digital encoding (eg. signed-magnitude, 12 or 2 s complement) of the data in the pay load of the RF frames, which encode the audio signal in the forward channel.

FIGS. 5A-5C illustrate a method, according to another embodiment of the present disclosure, in which the frame rate transmitted from the external unit 3 to the internal unit 5 is adapted/varied according to the instantaneous sound intensity and predicted demand in the implant's electrical power. The frame rate determined in DSP cluster 52 is, e.g., programmable.

FIG. 5C shows an example of an input audio signal 302. The x-axis 300 in FIGS. 5A-5C represents time. The input signal 302 is sampled at regular intervals, with samples [0]-[4] shown in the example. The sampling rate is at least twice the expected bandwidth of the audio signal 302. FIG. 5B shows the forward channel transmission at the default frame rate of the sound processor 8. Each sample is encoded into a respective frame (i.e., encoded sample [0], encoded sample [1], etc.) which is transmitted in turn by the RF transmitter 10 to the internal unit 5. In the example, each frame has a duration that is less than half of the time between samples.

FIG. 5A shows an example of a double-frame rate mode in which the data formatter 74 executes its operation at twice the default sampling rate, for example at 40 k frames/sec compared with a nominal rate of 20 kSamples/sec. In this double-frame mode, the data formatter 74 repeats each audio sample, i.e., outputs each audio sample twic. Thus, the encoded sample [0] is transmitted twice, etc. The data decoder 21 operates, e.g. at the default sampling rate so that the original data may be readily decoded. However, the double frame mode provides increased total RF energy to the internal unit 5.

The scalable frame rate adjustment might include, e.g, any integer multiples of the sampling rate of the audio signal. The double-frame rate is one example of the scalable frame rate. The scalable frame rate method might be implemented, e.g., such that the frame rate is constant in the short term, or in a multi-rate fashion to better match the estimated power demand in the implantable part of the system.

Alternatively, e.g., the data formatter 74 inserts audio samples which are zero-valued with every other data frame. The configuration of the data formatter 74 in regards to its mode of operation occurs via the supervising microcontroller 76 and changes in the configuration can be implemented, e.g., on-the-fly. The frame rate is based, e.g., on the audio intensity (power level) estimate which is calculated in the DSP cluster 52. Thus, for example, if a greater audio intensity is predicted, the frame rate is increased, and vice versa.

Figure 6A:
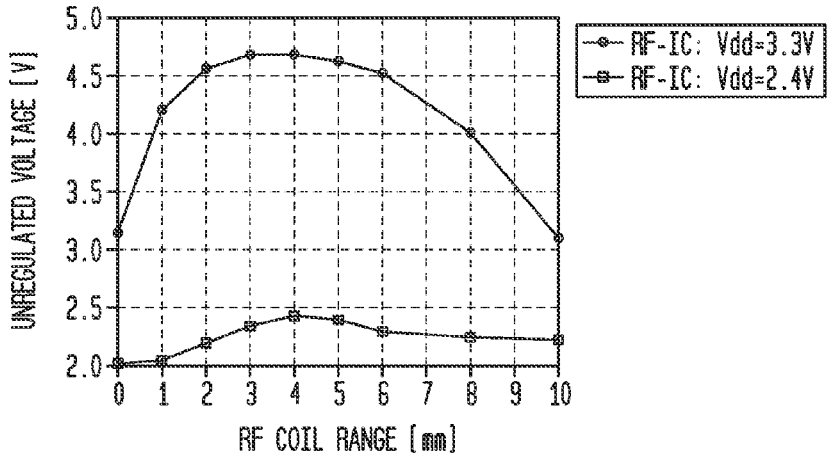
FIGS. 6A-6C are graphs plotting how the internal unit's unregulated voltage varies as a function of the link distance between the external and internal coils.

FIG. 6A are graphs plotting the characteristic of the unregulated voltage ($V_{DD}$) of the internal unit 5 as a function of the link distance d between the external coil 11 and the internal coil 17. Two curves are plotted, corresponding to two different values, e.g., 2.4V and 3.3V, of the supply voltage (RF IC Vdd) of the RF transmitter 10. In this graph, the sound processor 8 operates with a power level PL=100% in regards to the RF transmitter 10 power level, and the internal unit 5 processes a sinusoidal audio signal with a fundamental frequency of 1,000 Hz and an amplitude equal, to −6 dB relative the fell scale in the dynamic range of the digital signal 51.

Figure 6B:
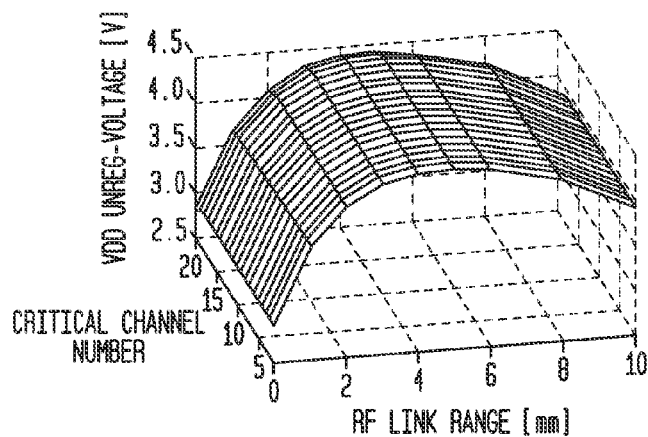
Figure 6C:
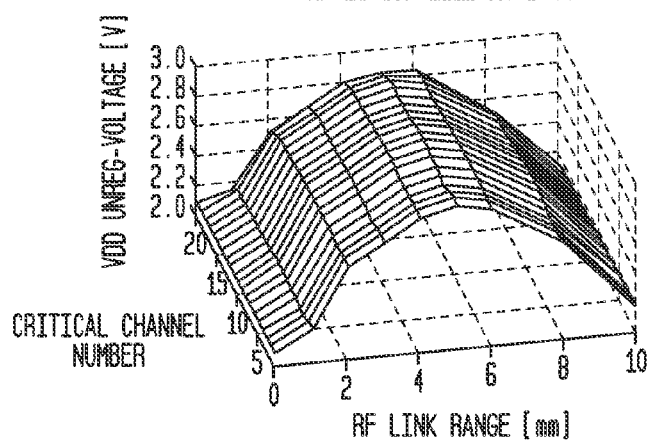

FIG. 6B is a 3D plot of the unregulated voltage 107 of the internal unit 5 as a function of link distance d, where RF IC Vdd is, e.g., 3.3V. The x-axis shows the link distance d in mm and the y-axis represents the audio band in the range of 100 to 10 kHz, expressed as critical bands 1 to 20. The z-axis shows the unregulated voltage 107 $V_{DD}$ of the internal unit 5. In these graphs, the loudness level is 120 dBSPL and wide band noise is used as a stimulus signal. FIG. 6C is a similar plot but shows the unregulated voltage 107 of the internal unit 5 as a function of d where the source voltage in the RF transmitter 10, RF IC Vdd is, e.g., 2.4V. In both FIGS. 6B and 6C, the unregulated voltage 107 of the internal unit 5 increases to a maximum as d increases and then falls as d increases further. The peak is sharper in the case shown in FIG. 6C, and occurs at a value of approximately 5 mm; this distance is the optimal distance for the illustrated implant example, and is determined by the RF coil geometry (shape, diameter) of the internal unit 5, the RF carrier frequency, and the equivalent electrical load of the internal unit 5 that is seen by the RF transmitter 10.

Figure 7:
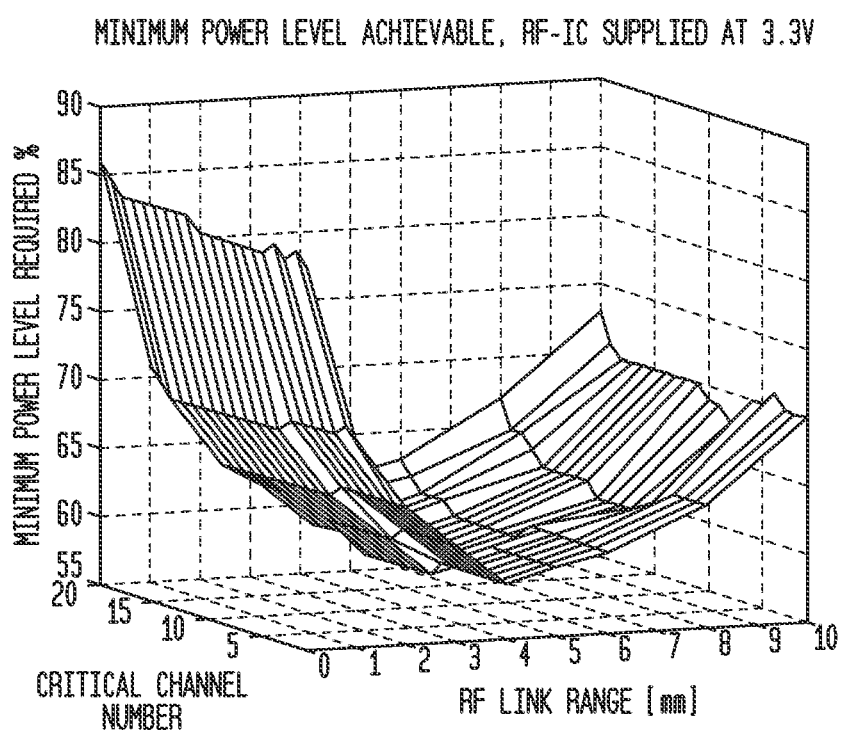
FIG. 7 is a graph plotting the minimum achievable power level in the external unit as a function of the link distance between the external and internal coils.

FIG. 7 is a three dimensional graph plotting the minimum achievable power level (PL) in the external RF transmitter 10, when the transmitter is supplied with maximum operating Voltage (e.g., Vdd=3.3V). The minimum achievable power is shown on the z-axis, in the range 55 to 90%. As in FIGS. 6A and 6B, the x-axis is the link distance d and the y-axis shows the critical bands used in the transmission. For low values of d, the achievable power level is relatively high, diminishing to a minimum level at around d of 5 mm. As d increases further, the achievable power level rises. To improve the utilisation of the battery 9, the power level setting is initially pre-set to a minimum value based on parameters such as those shown in FIG. 7. The power level setting gradually increases as the battery's energy depletes over time so that the implant's operation is sustained and free of temporal interruptions.

The power level adjustment is, for example, based on pulse width modulation of the signal that excites the tuned circuit in RF transmitter 10. The power level adjustment is implemented as an algorithm running in the DSP cluster 52. The link distance d is a parameter that is established during the implantation of the auditory prosthesis 1. Other critical parameters such as hearing and comfort thresholds are established by the clinician during the fitting session. The performance of the actuator 25 is characterized by its frequency response in the audible band and is expressed as the velocity magnitude over frequency. The actuator's efficiency (velocity output versus electrical power drawn) varies across frequencies and is affected by the actuator's resonance characteristic. Based on these parameters and the characteristic illustrated in FIGS. 6A to 6C, the output voltage of the voltage regulator supplying the sound processor 8 and the RF transmitter 10 is adjusted.

Other parameters that may be varied in response to predicted changes in signal levels relate to the RF signal 80. In one arrangement, e.g., the signal 80 transmitted from the external coil 11 to the internal coil 17 is an on/off modulated RF signal. The energy contained in the transmitted signal may be varied by increasing or decreasing the amplitude of the RF signal 80, for example by adjusting the tuned circuit in the RF transmitter 10. Alternatively, or in addition, the duty cycle of the on/off modulation (i.e., the width of the pulses output from the RF transmitter 10) is adjusted to vary the amount of energy transmitted to the internal unit 5.

This voltage adjustment is derived from a decision algorithm under consideration of: a) the constant operating parameters of the auditory prosthesis 1 for a given implant recipient such as the link distance d, recipient hearing and comfort thresholds, transducer efficiency/frequency response, and b) time-variant parameters such as present power-adjusting level setting, power demand indicated by the sound intensity algorithm, and the present life condition of the battery 9. The operation of the data encoder 74 may also be adjusted depending on the predicted intensity of the ambient sound.

The audio front end 50, e.g., includes a low-pass filter that limits the bandwidth of the input signal and an A/D converter that converts the filtered signal into the digital signal 51. In one arrangement, e.g., the A/D converter is a 16-bit circuit operating at 20 kHz. However, the sound processor 8 varies the number of bits used in the signal transmitted to the internal unit 5. For example, where there is a constant signal-to-noise ratio, if a high-intensity signal is being processed, 6 or 8 bits are used to represent the signal. If the signal intensity is lower, 12 or 16 bits are used to represent the signal.

The type of data encoding may also be varied. For example, two's complement encoding is used in general. An alternative is to use signed magnitude encoding, where a bit is used to indicate whether a number is positive or negative. The two's complement encoding may entail a higher member of bit transitions, which can lead to higher energy losses. Thus, in a lower energy mode the sound processor 8 may change to signed magnitude encoding of the digital data. Different types of digital coding with arbitrary code redundancy, varying disparity in zeros and ones can also be selected to encode the payload of the RF frames. The type of digital coding is selected dependent on the actual power demand in the implant electronics and the actuator load.

The adjustments in the system parameter settings in block 207 of method 200 can be determined by the same decision logic both for upward and downward adjustment. Alternatively, the adjustment characteristics may differ with regard to the time constant with which they are applied to the power adjusting circuits and parameters. Thus in one arrangement, e.g., the adjustment is more gradual in the downward direction and more rapid in the upward adjustment direction.

The step size of the new setting applied to the adjusting circuit depends on: the sound intensity measured relative to the current power level setting; expected power demand in the amplifier 23 and the actuator 25 for the current sound intensity; other processing sound parameters as audio signal gain, hearing and comfort thresholds; and auditory prosthesis 1 parameters such as RF coil coupling coefficient, skin flap thickness and implant operating voltage range.

The systems and methods described herein may improve the auditory prosthesis' continuous battery life by adjusting the power level as required by the individual recipient's fitting parameters, taking into account that the sound intensity modulates many power-consuming components in the prosthesis. The systems and methods disclosed herein may reduce the possibility of the recipient experiencing intermittencies in the auditory prosthesis' operation, which arise when the internal unit's average energy demand exceeds the average energy supplied by the external speech processor via the RF link.

The invention described and claimed herein is not to be limited in scope by the specific example embodiments herein disclosed, since these embodiments are intended as illustrations, and not limitations, of several aspects of the present invention. Any equivalent embodiments are intended to be within the scope of the present invention. Indeed, various modifications of the present invention in addition to those shown and described herein will become apparent to those skilled in die art from the foregoing description. Such modifications are also intended to fall within the scope of the appended claims.

The invention claimed is:

1. A method performed at an auditory prosthesis having an external unit and an internal unit for implantation in a recipient, the method comprising:
   capturing a sound signal;
   measuring one or more characteristics of the sound signal;
   processing the acoustic signal to generate encoded control signals representative thereof;
   transcutaneously transmitting a radio frequency (RF) signal according to the encoded control signals to the internal unit;
   with a decoder in the internal unit, decoding data from the transmitted RF signal;
   stimulating the recipient's auditory system based on the decoded data;
   adjusting at least one parameter of the auditory prosthesis that affects power consumption based on the at least one characteristic of the sound signal; and
   determining a step size for adjusting the at least one parameter, wherein an output of the decoder controls a linear velocity of the actuator, and the step size is dependent on a non-linear response characteristic of the actuator.

2. The method of claim 1, further comprising:
   transmitting the RF signal using an RF carrier, wherein the at least one parameter of the auditory prosthesis is an amplitude of the RF carrier.

3. The method of claim 1, further comprising:
   transmitting the RF signal using an on/off modulated RF carrier, wherein the at least one parameter of the auditory prosthesis is a duty cycle of the on/off modulated RF carrier.

4. The method of claim 1, further comprising:
   transmitting the RF signal as a sequence of frames, wherein the at least one parameter of the auditory prosthesis is a quantity of redundant frames interpolated into the transmitted signal.

5. The method of claim 1, further comprising:
   selecting a number of bits to use in providing the encoded control signals, wherein the at least one parameter of the auditory prosthesis is the selected number of bits.

6. The method of claim claim 5, wherein for a high-intensity acoustic level of the sound signal, the selected number of bits is in the range of 6 to 8 bits.

7. The method of claim 1, wherein:
   the type of data encoding is one of two's complement encoding and signed-magnitude encoding.

8. The method of claim 1, wherein:
   the at least one parameter of the auditory prosthesis is a type of data encoding used to generate the encoded control signals.

9. An auditory prosthesis comprising:
   an external unit including:
      a microphone to capture a sound signal;
      a sound processor to measure at least one characteristic of the sound signal and generates an encoded signal representative thereof; and
      a radio frequency (RF) transmitter to transmit an RF signal according to the encoded signal; and
   an internal unit, implantable in a recipient, including:
      a receiver to receive the RF signal and to extract energy therefrom for powering the internal unit;
      a decoder that decodes data from the transmitted signal; and
      an actuator that stimulates the recipient's auditory system based on the decoded data;
   the external unit further including:
      a controller to adjust the at least one parameter of the prosthesis that affects power consumption based on the at least one characteristic of the sound signal, wherein the controller is operable to determine a step size for adjusting the at least one parameter; and
   wherein an output of the decoder controls a linear velocity of the actuator;
   and the step size is dependent on a non-linear response characteristic of the actuator.

10. The auditory prosthesis of claim 9, wherein:
   the transmitted RF signal comprises an RF carrier, and the at least one parameter of the prosthesis is an amplitude of the RF carrier.

11. The auditory prosthesis of claim 9, wherein:
   the transmitted RF signal comprises an on/off modulated RF carrier, and the at least one parameter of the prosthesis is a duty cycle of the RF carrier.

12. The auditory prosthesis of claim 9, wherein:
   the external unit further comprises a voltage regulator to regulate voltage supply to the sound processor and the RF transmitter, and
   the at least one parameter of the prosthesis is an output voltage of the voltage regulator.

13. The auditory prosthesis of claim 9, wherein:
   the encoded signal comprises a sequence of frames, and the at least one parameter of the prosthesis is a quantity of redundant frames interpolated into the transmitted RF signal.

14. The auditory prosthesis of claim 9, wherein:
   the sound processor utilizes a selected number of bits in generating the encoded signal, and the at least one system parameter of the prosthesis is the selected number of bits.

15. The auditory prosthesis of claim 14, wherein:
   for a high-intensity acoustic level of the acoustic signal, the selected number of bits is in the range of 6 to 8 bits.

16. The auditory prosthesis of claim 14, wherein:
   for a low-intensity acoustic signal, the selected number of bits is in the range of 12 to 16 bits.

17. The auditory prosthesis of claim 9, wherein:
   the at least one system parameter is a type of data encoding used by the sound processor.

18. The auditory prosthesis of claim 17, wherein:
   the type of data encoding is one of two's complement encoding and signed-magnitude encoding.

19. The auditory prosthesis of claim 9, wherein:
the at least one system parameter is adjusted to increase an energy content of the transmitted signal if a current or predicted acoustic level of the acoustic signal increases.

20. The auditory prosthesis of claim 9, wherein the at least one system parameter is adjusted to decrease an energy content of the transmitted RF signal if one of a current or predicted acoustic level of the sound signal decreases.

21. The auditory prosthesis of claim 9, wherein:
the step size depends on whether the adjustment is an increase or a decrease of the system parameter.

22. The auditory prosthesis of claim 9, wherein:
the step size is dependent on a measured sound intensity of the sound signal relative to a current power setting.

23. The auditory prosthesis of claim 9, wherein:
the step size is dependent on an expected power demand in the actuator or an amplifier in the implantable part.

24. The auditory prosthesis of claim 9, wherein:
the step size is dependent on a characteristic of the recipient's fitting, including at least one of:
an RF coil coupling coefficient between the RF transmitter and the receiver;
the recipient's skin flap thickness; and
an operating voltage range of the internal unit.

25. The auditory prosthesis of claim 9, wherein:
the at least one parameter of the prosthesis is adjusted before the RF signal is transmitted.

26. The auditory prosthesis of claim 9, wherein:
a duration between capturing the acoustic signal and a corresponding activation of the actuator is less than about 10 ms.

27. The auditory prosthesis of claim 9, wherein:
the sound processor measures short term variations in the sound signal and monitors a long term intensity level of the sound signal.

* * * * *

UNITED STATES PATENT AND TRADEMARK OFFICE
CERTIFICATE OF CORRECTION

PATENT NO. : 9,980,057 B2  
APPLICATION NO. : 13/553804  
DATED : May 22, 2018  
INVENTOR(S) : Kostas Hatzianestis Page 1 of 1

It is certified that error appears in the above-identified patent and that said Letters Patent is hereby corrected as shown below:

In the Claims

Column 9, Line 65, Claim 6, remove "claim claim" and insert --claim--.

Signed and Sealed this
Sixth Day of November, 2018

Andrei Iancu
*Director of the United States Patent and Trademark Office*